US00PP08986P

United States Patent [19]

Fuess

[11] Patent Number: Plant 8,986

[45] Date of Patent: Nov. 22, 1994

[54] CHRYSANTHEMUM PLANT NAMED EMPIRE CHABLIS

[76] Inventor: Janet S. Fuess, 22 Country Club Dr., New York Mills, N.Y. 13417

[21] Appl. No.: 164,404

[22] Filed: Dec. 7, 1993

[51] Int. Cl.[5] ..... A01H 5/00

[52] U.S. Cl. ..... Plt./77

[58] Field of Search ..... Plt. 76, 77, 78, 82.1

[56] References Cited

U.S. PATENT DOCUMENTS

Plt. 6,775 5/1989 Hesse ..... Plt. 77

*Primary Examiner*—Howard J. Locker

*Attorney, Agent, or Firm*—Foley & Lardner

[57] ABSTRACT

A new and distinct cultivar of Chrysanthemum plant named Empire Chablis, characterized by the combined characteristics of creamy white outer ray florets and soft yellow center ray florets; almost fully double flowers; 6.5 to 7.0 cm capitulum diameter; seven week flower response in light/shade programs; natural season flowering date of August 25, and compact, cushion habit.

1 Drawing Sheet

1

The present invention comprises a new and distinct cultivar of *Chrysanthemum morifolium,* hereinafter referred to by the cultivar name Empire Chablis.

Empire Chablis is a product of a planned breeding program which had the objective of creating new Chrysanthemum cultivars having compact cushion habit, early flower response, large white decorative flowers, and a free branching habit, thereby making the new cultivar suitable for production as a garden variety.

Empire Chablis was originated from a hybridization made by the inventor Janet S. Fuess in a controlled breeding program in New Hartford, N.Y., in September 1988. Th female parent was Pink Champagne, disclosed in U.S. Plant Pat. No. 6,920. The male parent of Empire Chablis was a proprietary cultivar identified as B86-12, characterized by its yellow ray floret color and decorative flower form.

Empire Chablis was discovered and selected as one flowering plant within the progeny of the stated parentage by Janet S. Fuess in August 1989 in a controlled environment in New Hartford, N.Y.

The first act of asexual reproduction of Empire Chablis was accomplished when vegetative cuttings were taken from the initial selection in October 1989 in a controlled environment in New Hartford, N.Y., by a technician working under formulations established and supervised by the inventor. Horticultural examination of selected units initiated in August 1990 has demonstrated that the combination of characteristics as herein disclosed for Empire Chablis are firmly fixed and are retained through successive generations of asexual reproduction.

Empire Chablis has not been observed under all possible environmental conditions. The phenotype may vary somewhat with variations in environment such as temperature, light intensity, and daylength, without, however, any variation in the genotype.

The following observations, measurements and comparisons describe plants grown in New Hartford, N.Y., under natural outdoor conditions which approximate those generally used in commercial practice.

The following traits have been repeatedly observed and are determined to be basic characteristics of Empire Chablis which in combination distinguish this Chrysanthemum as a new and distinct cultivar.

2

1. Creamy white outer ray florets with soft yellow center ray florets.
2. Almost fully double flowers, with an average of 22 disk florets being observed.
3. Flowers very resistant to shattering.
4. Fully expanded ray florets are approximately 2.8 cm long and 0.8 cm wide.
5. Average of 229 ray florets and 22 disc florets per flower.
6. Capitulum is 6.5–7.0 cm in diameter.
7. A 7 week flower response in light/shade programs.
8. A natural season flowering date of August 25 when grown in New Hartford.
9. Compact, cushion habit, making it suitable for production in 4" to 8" containers.

Of the many commercial cultivars known to the present inventor, the most similar in comparison to Empire Chablis is Tolima, disclosed in U.S. Plant Pat. No. 6,988. In comparison to Tolima, Empire Chablis has a slightly more upright habit, yellow center ray florets, compared to the yellow-green (150D) center ray florets of Tolima, and a much earlier natural season flowering date. The seven weeks response time in light/shade programs, white outer ray florets, and large capitulum diameter of Empire Chablis are similar to those same characteristics of Tolima.

The accompanying photographic drawings show typical inflorescence and foliage characteristics of Empire Chablis, with colors being as nearly true as possible with illustrations of this type.

The top illustration is photo comprising a top perspective view of Empire Chablis grown in a pot.

The bottom illustration is a photo comprising a top view showing in greater detail buds and open flowers of Empire Chablis.

In the following description color references are made to The Royal Horticultural Society Colour Chart. The color values were determined between 2:00 and 4:00 PM on Sep. 20, 1993 under 4,000 foot candles light intensity at New Hartford, N.Y.

Classification:

*Botanical.*—*Dendranthema grandiflora* cv Empire Chablis.

*Commercial.*—Garden and greenhouse mum.

INFLORESCENCE

A. Capitulum:
*Form.*—Decorative
*Diameter across face.*—6.5–7.0 cm.

B. Corolla of ray florets:
*Color (general tonality from a distance of three meters).*—White.
*Color (upper surface).*—Outer florets 155D; center florets 3C.
*Color (under surface).*—Outer florets 155D; center florets 3C.

C. Corolla of disc florets:
*Color (mature).*—7A.
*Color (immature).*—5A.

D. Reproductive organs:
*Androecium.*—Present on disc florets only; 5 stamens, 0.3 cm; filaments separate; anther sacs connected and completely enclosing stigma.
*Gynoecium.*—Ray: Style 0.6 cm, bifurcated. Disc: Style, 0.3 cm, bifurcated, enclosed in anther ring.

PLANT

A. General appearance:
*Height.*—25–35 cm, when mature and grown in an 8″ container.

B. Foliage:
*Color (upper surface).*—137A.
*Color (lower surface).*—137C.
*Shape.*—five lobed.
*Size.*—6–8 cm long, and 4.5–5.5 cm wide.

It is claimed:

1. A new and distinct cultivar of Chrysanthemum plant named Empire Chablis, as illustrated and described.

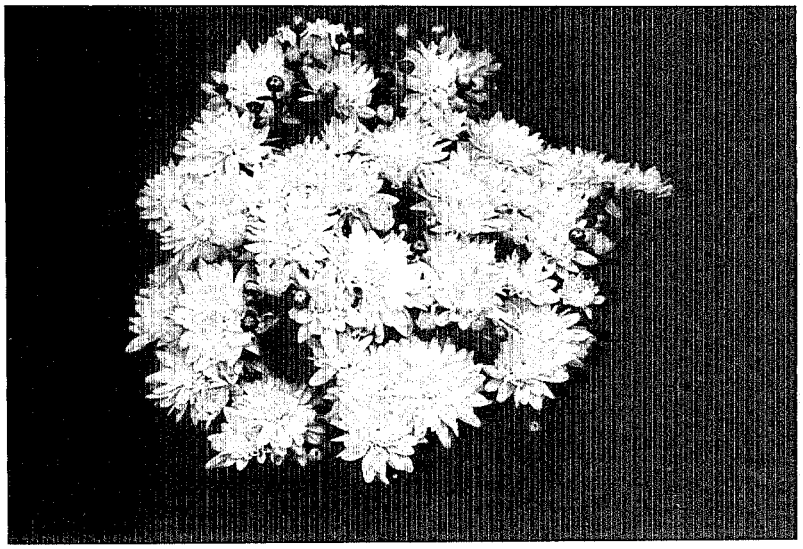
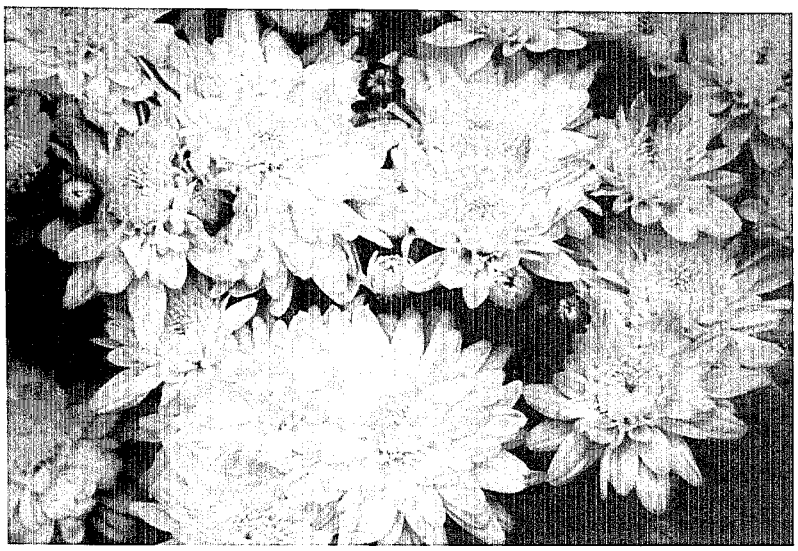

* * * * *